United States Patent [19]

Panzer

[11] 4,077,917

[45] * Mar. 7, 1978

[54] AQUEOUS SOLUBLE MIXED COMPLEX ORGANIC SALTS OF ALUMINUM SULFATE

[75] Inventor: George W. Panzer, Timonium, Md.

[73] Assignee: Alcolac, Inc., Baltimore, Md.

[*] Notice: The portion of the term of this patent subsequent to Oct. 7, 1992, has been disclaimed.

[21] Appl. No.: 610,933

[22] Filed: Sep. 8, 1975

Related U.S. Application Data

[63] Continuation-in-part of Ser. No. 365,803, May 31, 1973, Pat. No. 3,910,978.

[51] Int. Cl.$^2$ .......................... C11D 1/12; C07F 5/06
[52] U.S. Cl. .................................. 252/545; 252/548; 252/550; 252/551; 252/554; 252/557; 252/558; 260/448 R; 260/458 R; 260/505 N; 260/458 C; 260/513 R
[58] Field of Search ............... 252/550, 551, 554, 557, 252/558, 545, 548

[56] References Cited

U.S. PATENT DOCUMENTS

| | | | |
|---|---|---|---|
| 2,304,230 | 12/1942 | Archibald | 252/353 |
| 2,757,193 | 7/1956 | Zoppa | 260/503 |
| 2,766,212 | 10/1956 | Grifo | 252/551 |
| 3,011,977 | 12/1961 | Raecke | 252/550 |
| 3,133,946 | 5/1964 | Maurer et al. | 260/439 |
| 3,910,978 | 10/1975 | Panzer | 260/448 R |

Primary Examiner—P.E. Willis, Jr.
Attorney, Agent, or Firm—Finnegan, Henderson, Farabow & Garrett

[57] ABSTRACT

Mixed complex organic salts of aluminum sulfate are prepared. The mixed complex salts are soluble in aqueous solutions and have surface active properties. The organic portion of the mixed salts is derived from a member selected from the group of a neutralized salt of an aliphatic alcohol sulfate; an alkylaryl sulfate; an alkyl, aryl, or alkylaryl sulfonate; a dialkyl or alkyloxyalkylene sulfosuccinate; an N-acyl-N-alkyl taurate; a sulfoalkyl ester of a fatty acid; and a sulfated ethylene oxide-propylene oxide block copolymer. Ethylene oxide, propylene oxide, or butylene oxide, or polymers thereof, can be introduced into the organic portion of the mixed salt to obtain a mixed complex aluminum salt which is completely soluble upon any degree of dilution. Non-ethoxylated salts, non-propoxylated and non-butoxylated salts become insoluble upon dilution at specific dilution points depending on the cation of the neutralized salt used to form the mixed complex salt.

18 Claims, No Drawings

AQUEOUS SOLUBLE MIXED COMPLEX ORGANIC SALTS OF ALUMINUM SULFATE

RELATED APPLICATIONS

This application is a continuation-in-part of Applicant's copending application Ser. No. 365,803, filed May 31, 1973, entitled Aqueous Soluble Mixed Complex Salts of Aluminum Aliphatic Alcohol Sulfates, now U.S. Pat. No. 3,910,978.

FIELD OF INVENTION

This invention relates to soluble aluminum salts and their method of preparation, and more particularly, to mixed complex organic salts of aluminum sulfate.

BACKGROUND OF INVENTION

The prior art has taught that soluble products having many useful properties, especially strong surface active properties can be obtained by combining the alkali metals, or ammonia, or ethanolamine or certain other organic bases with the sulfated compounds of high molecular weight aliphatic alcohols. These compounds usually have good wetting, sudsing, emulsifying and/or detergent properties. Alkali metal products of this type are soluble in water which make them especially useful in detergent compositions. Heavy metal salts, as opposed to alkali metal salts of the above sulfonated compounds, are not predictable in their solubility behavior in aqueous solutions and are often insoluble.

The prior art does recognize, however, that some heavy metal sulfonated salts are soluble in aqueous solutions, but aluminum salts are not known for their solubility. For example, it is known that aluminum lauryl sulfate is insoluble in an aqueous solution. Thus, Shigeru Miyamoto in his article "The Effect of Metallic Ions On Surface Chemical Phenomena LL," Mem. Fac. Sci. Kyushu University, Series C, Vol. III, No. 3, 1960, reports the solubility of aluminum dodecyl sulfate as being only $9.25 \times 10^{-5}$ moles per kg $H_2O$. The article describes the preparation of aluminum dodecyl sulfate by mixing $5 \times 10^{-4}$ liters of pure sodium dodecyl sulfate with pure aluminum chloride. This procedure, however, leads to an insoluble form of aluminum lauryl sulfate.

SUMMARY OF THE INVENTION

In accordance with the present invention, it has been found that novel organic aluminum salts that are soluble in water can be prepared which are mixed complex metal salts of aluminum sulfate and a neutralized salt of an organic compound. The organic compound is selected from the group consisting of an aliphatic alcohol sulfate; an alkylaryl sulfate; an alkyl, aryl or alkylaryl sulfonate; a dialkyl or alkyloxyalkylene sulfosuccinate; an N-acryl-N-alkytaurate; a sulfoalkyl ester of a fatty acid, e.g., an isethionate; and a sulfated ethylene oxide-propylene oxide block polymer. As discussed more fully hereinbelow, the neutralized salts of the sulfates, sulfonates, sulfosuccinates, taurates and isethionates used to prepare the aluminum salts of the present invention may be ethoxylated, propoxylated or butoxylated.

The soluble mixed complex salts of the present invention which are prepared from neutralized salts of an aliphatic alcohol sulfate, an alkylaryl sulfate, an alkyl, aryl or alkylaryl sulfonate, a dialkyl or alkyloxyalkylene sulfosuccinate, an N-acyl-N-alkyltaurate, a sulfoalkyl ester of a fatty acid, and oxyalkylene derivatives thereof have the general formula I:

$$[R-(OC_yH_{2y})_n-A_m-(O)_p-SO_3]_xM \cdot I[Al_2(SO_4)_3] \qquad \text{I.}$$

in which R is an aliphatic radical containing 1 to 30 carbon atoms or alkylaryl hydrophobic residue having an alkyl radical containing 1 to 30 carbon atoms; $n$ is the number of alkylene oxide groups and can be from 0 to about 100; $y$ is a number from 2 to 4; A is a radical selected from the group consisting of:

(i)

(ii)

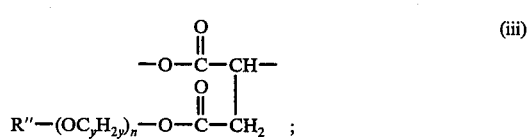

(iii)

$R'$ is H or an alkyl group of 1 to 4 carbon atoms; $R''$ is an alkali metal or an alkyl group having from 8 to 22 carbon atoms; $m$ and $p$ are each the numbers 0 or 1, M is a cation having a valence of $x$, and generally is an alkali metal, alkaline earth metal (including magnesium), manganese, zinc, copper, iron, cobalt, nickel, or a nitrogen containing base such as ammonia, ethanolamine, and the like; $x$ is the hydrogen equivalence value of M and can be 1 or 2; and I can be a number from about 0.001 to about 6.

The soluble mixed complex salts of the present invention which are prepared from the neutralized sulfates have the general formula II:

$$[R-(OC_yH_{2y})_n-OSO_3]_xM \cdot I[Al_2(SO_4)_3]. \qquad \text{II.}$$

in which R, $y$, $n$, $x$, M and I are the same as previously defined in connection with Formula I.

The soluble mixed complex salts which are prepared from the sulfated ethylene oxide-propylene oxide block polymers can be represented by the following formula III:

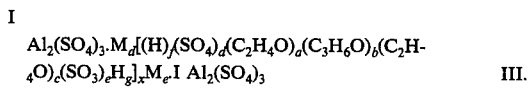

$$Al_2(SO_4)_3 \cdot M_d[(H)_f(SO_4)_d(C_2H_4O)_a(C_3H_6O)_b(C_2H_4O)_c(SO_3)_eH_g]_xM_e \cdot I \; Al_2(SO_4)_3 \qquad \text{III.}$$

in which $b$ is an integer from 15 to 60; $a$ and $c$ are each at least 1 and $a+c$ is an integer from 4 to 300; M, $x$ and I are the same as defined above in connection with Formula I; $f+d$ and $e+g$ are equal to 1; and $d$ and $e$ are each a number from 0.1 to 1.0.

The present invention provides aqueous solutions which contain from about 10 to about 60%, and preferably 10 to 35%, of the above novel soluble salts, based on the total weight of the solution.

The present invention also provides a method of preparing the soluble mixed complex organic aluminum salts which comprises adding aluminum sulfate to a concentrated aqueous solution of the selected neutralized salt of the organic portion of the mixed complex salt to be formed. The concentration of the aqueous solution of the neutralized salt is between about 10 to 60%. If the solution of the neutralized salt is too dilute, the addition of the aluminum sulfate will result in the formation of a precipitate and the soluble mixed complex organic aluminum salts of the present invention will not be formed.

When the neutralized salt of an aliphatic alcohol sulfate is used to prepare the novel aluminum salts of the present invention, and the salt is ethoxylated, propoxylated or butoxylated prior to being mixed with the aluminum sulfate, the novel aluminum salts are found to be completely soluble in water at substantially all concentrations or degrees of dilution. Complete solubility in water at substantially all concentrations or degrees of dilution is also a characteristic of the novel aluminum salts prepared from neutralized ethoxylated, propoxylated, or butoxylated sulfosuccinates and from neutralized sulfated ethylene oxide-propylene oxide block polymers.

The degree of alkoxylation necessary to bring about the solubilization at high degrees of dilution varies with the number of carbon atoms in the organic radical, with a greater degree of ethoxylation, propoxylation or butoxylation being required as the number of carbon atoms increases. When the neutralized salt does not contain any ethoxy, propoxy or butoxy groups, however, the aqueous solution of the soluble aluminum salts can be diluted to a point where a novel precipitate forms. For example, when the neutralized complex salt is formed by adding aluminum sulfate to an aliphatic alcohol sulfate, the precipitate is an insoluble aluminum aliphatic alcohol sulfate having the general formula IV:

$$[R - OSO_3]_q Al \cdot Z[M_r(OSO_4)_x] \quad \text{IV.}$$

in which R and M are defined as above, $q$ is from 0.167 to 6; Z is from 0 to 1; $r$ is 1 or 2; $r$ is 1 when $x$ is 2 and $r$ is 2 when $x$ is 1. The point where the precipitate forms is specific for each salt so that the formation of the precipitate can be controlled and obtained whenever it is desired. The precipitate can contain small amounts of ethoxy, propoxy or butoxy groups when higher aliphatic alcohols are used.

The aqueous solutions of the present invention have valuable surface active properties, excellent substantivity, emulsifying and foaming properties, and are compatible with foam boosters. The solutions can be used in composition for hair and skin cosmetics, detergents and cleansers, laundry aides and washes, textile processing and dyeing and other useful applications.

DESCRIPTION OF PREFERRED EMBODIMENTS

In accordance with the invention, the soluble mixed complex salt of the present invention is formed by mixing aluminum sulfate with an aqueous solution of a neutralized salt of an organic member selected from the group consisting of an aliphatic alcohol sulfate; an alkylaryl sulfate; an alkyl, aryl, or alkylaryl sulfonate; a dialkyl or alkyloxyalkylene sulfosuccinate, such as an alkylethoxy sulfosuccinate; an N-acyl-N-alkyl taurate; a sulfoalkyl ester of a fatty acid; and a sulfated ethylene oxide-propylene oxide block polymer. The aluminum sulfate is commercially obtainable as a solid and can be added as such to the aqueous solution of the neutralized aliphatic alcohol sulfate, or preferably can be added as an aqueous solution. If an aqueous solution of aluminum sulfate is used, it preferably contains 5 to 50 weight percent of aluminum sulfate, based on the weight of the solution. The aqueous solution of selected neutralized organic members preferably contain 10 to 60% of neutralized organic member, based on the weight of the solution. The concentrations of the solutions are chosen so that the final solution will have an active theory content of the mixed complex organic aluminum salt of between about 10 to 60%, and preferably 10 to 35%.

The addition of the aluminum sulfate to the aqueous solution of the neutralized salt of the selected organic member is carried out preferably at room temperature to about 50° C with stirring.

The neutralized salt of the selected organic member used in the present invention can be prepared in accordance with known techniques. For example, the neutralized alkyl, aryl and alkylaryl sulfonates are formed by neutralizing the corresponding sulfonic acid with an appropriate base such as a metal hydroxide or oxide. The sulfonic acids which are subjected to neutralization may be prepared by various well known techniques, including the direct sulfonation of alkanes, alkenes, aryl compounds, such as benzene, toluene phenol and the like, and alkyl substituted benzenes, napthalenes and the like with sulfuric acid, oleums of various strengths, and $SO_3$. Thus, among the sulfonates contemplated for use in the present invention are the hexyl sulfonates, nonyl sulfonates, decyl sulfonates, lauryl sulfonates, oleyl sulfonates, carnaubyl sulfonates; branched chain octyl, decyl, dodecyl, tridecyl, tetradecyl, hexadecyl and octadecyl aliphatic sulfonates as, for example, the 2-ethyl hexyl sulfonates, 2-n butyl octyl sulfonates, 2-butyl tetradecyl sulfonates; and, in general, the higher molecular weight saturated and unsaturated aliphatic straight chain and branched chain sulfonates; alkyl aryl sulfonates as, for example, the dodecyl benzene sulfonates, tridecyl benzene sulfonates, nonyl benzene sulfonates, isopropyl napthalene sulfonates, nonyl napthalene sulfonates and the like; and any sulfonates such as the benzene sulfonates. Preferably, the sulfonic acids which are utilized are those having alkyl groups corresponding to the fatty acids occurring in triglyceride oils and fats of vegetable or animal origin, natural or hydrogenated, such as corn oil, cottonseed oil, sesame oil, coconut oil, palm kernel oil, sunflower seed oil, lard, tallow, soya bean oil and the like, with those sulfonic acids having alkyl groups containing from 8 to 22 carbons being preferred.

The neutralized sulfonates of these sulfonic acids may be represented by the formula V:

$$(R - SO_3)_x M \quad \text{V.}$$

in which R is an alkyl, aryl or alkylaryl residue containing from 1 to 30 carbon atoms in the alkyl chain. M represents a cation or the residue of a salt forming compound such as sodium, potassium, ammonium, monoethanolamine or the like, and $x$ is a small whole number, at least 1.

The neutralized aliphatic alcohol sulfates and alkyl aryl hydrophobe sulfates are formed by neutralizing aliphatic or alkyl aryl sulfuric acids known as acid sulfates, with an appropriate base such as a metal hydroxide or oxide. The acid sulfates are prepared by sulfating aliphatic straight or branched chain alcohols, alkyl phenols and ethoxylated alkyl phenols such as hexyl alcohol, heptyl alcohol, octyl alcohol, nonyl alcohol, decyl alcohol, undecyl alcohol, lauryl alcohol, myristyl alcohol, cetyl alcohol, oleyl alcohol, linoleyl alcohol, stearyl alcohol, ricinoleyl alcohol, palmitoleyl alcohol, melissyl alcohol, ceryl alcohol, carnaubyl alcohol, myricyl alcohol, hexyl phenol, heptyl phenol, octyl phenol, nonyl phenol, decyl phenol, undecyl phenol, ceryl phenol, 2 ethyl-hexyl phenol, 2-n butyl-octyl phenol, 2-butyl tetradecyl phenol, nonyl ethoxy phenol, hexyl ethoxy phenol, decyl ethoxy phenol; branched chain octyl, decyl, dodecyl, tridecyl, tetradecyl, hexadecyl and octadecyl aliphatic alcohols as, for example, 2-ethyl hexanol-1, 2-n butyl octanol-1, 2-butyl tetradecanol-1; and, in general, the higher molecular weight saturated and unsaturated aliphatic straight chain and branched chain alcohols and alkyl substituted phenols.

Preferably, the aliphatic alcohols and the alkyl substituted portions of the alkyl substituted phenols and ethoxylated alkyl phenols which are utilized are those corresponding to the fatty acids occurring in triglyceride oils and fats of vegetable or animal origin, natural or hydrogenated, such as corn oil, cottonseed oil, sesame oil, coconut oil, palm kernel oil, sunflower seed oil, lard, tallow, soya bean oil and the like with the alcohols and alkyl groups containing from 8 to 22 carbon atoms being preferred. Other alcohols which may be employed are the cyclo aliphatic or alicyclic alcohols such as the sterols as, for example, cholesterol, iso-cholesterol, phytosterol, silisterol, and such unsaturated alcohols as linalool, citroneloil, geranoil and the like and hydrogenation products of the foregoing. Also included within the class of alcohols which may be employed are such compounds as the hydroxy and alpha-hydroxy higher aliphatic and fatty acids, for example, ricinoleic acid, alpha-hydroxy stearic acid, alpha-hydroxylauric acid, di-hydroxy stearic acid, i-hydroxy-stearic acid, alpha-hydroxy palmitic acid, and the like, as well as esters of hydroxy-fatty acids, such as ethyl ricinoleate, castor oil, butyl alpha-hydroxystearate, cetyl hydroxystearate, and the like.

The term "alcohols," as employed herein, is intended to include alcohols which may or may not contain other groups such as carboxylic, halogen, sulfonic, sulfate, or other radicals. The alcohols obtainable by substituting alkyl or acyl radicals, preferably of high molecular weight, in place of the hydrogen of one or more hydroxy groups of polyhydroxy substances or polyhydric alcohols, it being understood that at least one hydroxy group attached to the nucleus of the polyhydroxy substance or polyhydric alcohol remains, are also within the scope of the alcohols from which the sulfates may be produced.

As examples of such alcohols may be mentioned, partially esterified or partially etherified, sugars and sugar alcohols such as monolauric acid ester of sucrose, monostearic acid ester of dextrose, monopalmitic acid ester of mannitol, dicaproic acid ester of maltose, mono-octyl ether of sorbitol, monolauryl ether of pentraerythritol, monolauric acid ester of pentaerythritol, and the like; the monoglycerides and diglycerides, preferably of the higher fatty acids, as, for example, monolauric, monomyristin, monostearin, distearin, diolein, decaproin, monolauryl ether of glycerol, ci-cetyl ether of glycerol, monostearic acid ester of diethylene glycol, monolauric acid ester of ethylene glycol, and the like.

It is, of course, obvious that the alcohols and the alkyl and hydrophobes from which the sulfates may be produced may be prepared in accordance with any desired method. For example, many of them may be prepared by the so-called Bouveault and Blanc method, or alternatively, by the reduction or catalytic reduction with hydrogen or natural or hydrogenated animal or vegetable fats and oils, or mixtures thereof, in accordance with well known practices. Again, they may be derived from synthetic processes such as by the oxidation of hydrocarbons or may be prepared by saponification of waxes and the like. Alternatively, they may be prepared by reduction of aldehydes or by the Grignard reaction.

It is likewise apparent that mixtures of the foregoing or other alcohols and alkyl aryl hydrophobes may be utilized in the preparation of the sulfates as, for example, the mixture of alcohols resulting from the hydrogenation of coconut oil or the free fatty acids of coconut oil. Such a hydrogenation produces an alcohol mixture where lauryl alcohol comprises about 45% of the total alcohol mixture, the remaining alcohols running from $C_4$ to $C_{18}$. Again, mixtures of alcohols such as are present in the so-called sperm oil alcohols, as well as those present in wool-fat, may equally efficaciously be utilized. Indeed, these higher molecular weight alcohols are generally offered on the market in the form of mixtures of different alcohols. If desired for any specific purpose, special fractions which predominate in a certain particular higher molecular weight alcohol may be utilized or, if so desired, the products may be prepared from a single, substantially pure alcohol.

The neutralized sulfates of these aliphatic alcohols and alkyl aryl sulfates may be represented by the formula VI:

$$(R - O - SO_3 -)_x M \qquad \text{VI.}$$

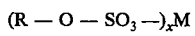

in which R represents the residue of an aliphatic alcohol or alkyl aryl hydrophobe containing from 1 to 30 carbon atoms. M represents a cation or the residue of a salt-forming compound such as sodium, potassium, ammonium, mono-ethanolamine or the like, and $x$ is a small whole number, at least one.

The neutralized sulfates described above are usually prepared from the acid sulfates by neutralizing the acid sulfate by anti-acid materials and, in this connection, considerable latitude and modification may be exercised. In general, inorganic as well as organic anti-acid agents may be employed, examples of which are carbonates, bicarbonates and hydroxides of the alkali metals (including ammonium), sodium oxide, ammonia gas, magnesium oxide, magnesium carbonate, organic anti-acid nitrogenous materials including amines, alcohol and alkylol amines such as, for example, mono-, di and triethanolamine and mixtures thereof, propanolamines, butanolamines, polynitrogenous amines such as ethylene diamine, ethylene triamine and the like, pyridine, methylpyridine, piperidine, quaternary ammonium bases such as tetraethyl ammonium hydroxide, tetramethyl ammonium hydroxide, and in general, primary, secondary and tertiary amines substituted or not with other radicals such as hydroxy, alkyl, aryl, cycloalkyl groups, and the like. It will be understood that by the term "cation," as used herein, is meant such elements as have been mentioned and, in general, atoms or radicals which are regarded as bearing a positive charge or capable of replacing acidic hydrogen. The reaction products may be neutralized to any extent desired as, for example, to methyl orange, litmus or phenolphthalein. The sulfates referred to hereinabove are described, among other places, in the following U.S. Pat. Nos. 1,897,741; 1,968,793; 1,968,794; 1,968,796; 1,968,797; 2,006,309; 2,023,387; 2,052,027; and 2,077,005.

As indicated above, the neutralized sulfate salts used to prepare the novel soluble organic aluminum salts of the present invention can be ethoxylated, propoxylated or butoxylated. These ethoxylated, propoxylated or butoxylated neutralized salts can be prepared by first condensing the aliphatic alcohol or alkyl aryl alcohol with ethylene oxide, propylene oxide, or butylene oxide (including mixtures of the oxyalkylenes) and sulfating the product thus obtained. For example, technically pure lauryl alcohol can be ethoxylated by using an amount of ethylene oxide corresponding to the desired average number of ethoxy groups. The ethoxylated alcohol is then sulfated, and the sulfated product is neutralized with an appropriate base such as sodium hydroxide as described above. When ethoxy, propoxy, or butoxy groups are introduced into the neutralized salt, $n$ in formula I is from about 0.5 to 100, and preferably is between about 1 to 50.

When the ethoxy, propoxy or butoxy groups are present in the neutralized salt, the resulting aqueous solution of the soluble, complex mixed organic aluminum salts of this invention generally can be diluted with water to any degree of dilution without formation of an insoluble precipitate. The degree of ethoxylation, propoxylation or butoxylation necessary to bring about the solubilization of the complex mixed organic aluminum salts increases as the molecular weight of the aliphatic radical increases. For example, a mixed, complex aluminum aluryl sulfate can be diluted to practically any degree of dilution when it contains an average of about one ethoxy group or one propoxy group per molecule whereas a myristyl salt usually needs a greater number of ethoxy, propoxy or butoxy groups such as about three to six per molecule to be soluble at all degrees of dilution. When no ethoxy, propoxy or butoxy groups are introduced into the neutralized sulfates, the resulting mixed complex organic aluminum salts of this invention are soluble in water at concentrations of from about 10 to 60 percent. When these concentrated aqueous solutions are diluted, however, insoluble precipitates will form.

The neutralized sulfosuccinates contemplated for use in preparing the novel mixed complex salts of aluminum sulfate are the commercially available dialkyl sulfosuccinates and alkyloxyalkylene sulfosuccinates, especially the sodium dialkyl sulfonates of the type sold under the Aerosol, Duowet, Monowet, Nekal, Shercowet and Tex-Wet Trademarks. The neutralized dialkyl sulfosuccinates may be represented by the formula VII:

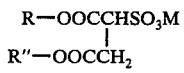

VII.

in which R" represents an alkali metal or an alkyl group, having from 8 to 22 carbon atoms, and M and R are as previously defined.

Examples of suitable sulfosuccinates include sodium diamyl sulfosuccinate, sodium dihexyl sulfosuccinate, sodium di (2-ethylhexyl) sulfosuccinate, sodium dioctyl sulfosuccinate and sodium diisobutyl sulfosuccinate.

Ethoxylated, propoxylated and butoxylated sulfosuccinates can also be used and, as is the case with the ethoxylated, propoxylated and butoxylated sulfates, the ethoxylated, propoxylated and butoxylated sulfosuccinates form mixed complex organic salts with aluminum sulfate which are infinitely soluble in water, whereas non-ethoxylated, non-propoxylated and non-butoxylated sulfosuccinates form complex salts which precipitate upon dilution.

The neutralized alkyloxyalkylene sulfosuccinates may be represented by the formula VIII:

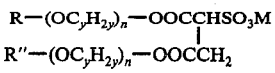

VIII.

in which R, R", $y$, $n$ and M are as previously defined.

Specific examples of ethoxylated sulfosuccinates which are suitable for use in preparing the mixed complex organic salts of the present invention are disodium dioctylethoxy sulfosuccinate, disodium dihexylethoxy sulfosuccinate and disodium di (2-ethylhexyl) ethoxy sulfosuccinate.

The neutralized taurates which may be used to prepare the present mixed complex organic salts of aluminum sulfate include the commercially available N-acyl-N-alkyl taurates which may be represented by the formula IX:

IX.

in which R, R' and M are as previously defined. Thus, suitable neutralized taurates include sodium N-oleoyl-N methyltaurate, sodium N-cocoacyl-N-methyltaurate, sodium N-palmitoyl-N-methyltaurate, sodium N-tall oil-N-methyl-taurate, sodium N-palmitoyl-N-cyclohexyltaurate, sodium N-oleoyl-N-ethyltaurate, sodium N-methyl-N-coconut oil taurate and the like.

The neutralized salts of sulfoalkyl esters of fatty acids which may be used to prepare the present mixed complex organic salts of aluminum sulfate may be represented by the formula X:

$$RCOOC_yH_{2y}SO_3M \qquad \qquad X.$$

in which R, $y$, and M are as previously defined. Preferred compounds of this type are the sodium salts of the 2-sulfoethyl esters of fatty acids which can be prepared commercially from sodium isethionate (obtained by the reaction of ethylene oxide with a concentrated solution of sodium bisulfite) and a fatty acid or acyl chloride. The reaction between the acyl chloride and the sodium isethionate is carried out in the absence of water or solvent under vacuum in a heavy duty mixer. After the total charge is added to the reactor and brought to temperature, HCl is rapidly evolved, leaving the finely divided sodium salt of the 2-sulfoester. Examples of suitable neutralized isethionates include sodium coconut oil isethionate, sodium tallow isethionate, sodium corn oil isethionate, sodium palm kernel oil isethionate, sodium tall oil isethionate, and the like.

The neutralized sulfated ethylene oxide-propylene oxide block polymers which are suitable for preparing the novel mixed complex organic aluminum sulfates may be prepared by reacting propylene oxide with propylene glycol to form a series of polyoxypropylene hydrophobes having molecular weights ranging from about 950 to about 3250. These hydrophobes are then solubilized by ethoxylation to polyoxyethylene contents that range from about 20 to 90% of the total weight. Such block copolymers are commercially available as Pluronics.

The ethylene oxide-propylene oxide block polymers are then sulfated with sulfuric acid, oleum or sulfur trioxide under conventional conditions to form the free acids, which acids are then neutralized to form the desired salts. The soluble mixed complex organic salts of aluminum sulfate which are prepared from the sulfated block polymers may be represented by the formula III:

I

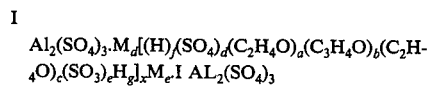
$Al_2(SO_4)_3 \cdot M_d[(H)_f(SO_4)_d(C_2H_4O)_a(C_3H_4O)_b(C_2H_4O)_c(SO_3)_eH_g]_xM_e \cdot I\ Al_2(SO_4)_3$ in which $a$ and $c$ are each greater than one and $a+c$ represents an integer from 4 to 300; $b$ represents an integer from 15 to 60, $f+d$ and $e+g$ equal one; $d$ and $e$ represent a number from 0.1 to 1.0; and M, $x$ and I have the same meaning as in formula I.

As is the case with the ethoxylated and propoxylated neutralized sulfates and sulfosuccinates, the sulfated ethylene oxide-propylene oxide block polymers form complex salts with aluminum sulfate which are infinitely soluble in water.

The concentrations of the aqueous solutions of neutralized sulfonates, succinates, taurates, sulfoalkyl esters of a fatty acid, ethylene oxide-propylene oxide block polymers and sulfates used to prepare the novel mixed complex organic aluminum salts of the present invention are chosen in relation to the moles of aluminum sulfate that are to be used so that the number of moles of aluminum sulfate per mole of neutralized salt is between about 0.001 to 6. Preferably, chemical equivalent weight amounts of the aluminum sulfate and neutralized salt are used. For example, 1 mole of sodium lauryl sulfate is a chemical equivalent amount of 1/6 of a mole of aluminum sulfate.

The aqueous compositions of the present invention can be used in a variety of cosmetic compositions such as shampoos, skin care products and bath products to provide a skin or hair conditioning effect. The aqueous compositions also have valuable bacteriocidal, fungicidal and astringent properties and thus can be used in a variety of pharmaceutical as well as cosmetic products. The aqueous compositions are also valuable as lubricants and dyeing aids for textile fibers.

The aqueous solutions also have valuable detergent properties. The aqueous solutions are often diluted in use so that the insoluble precipitates of this invention are formed which contribute to the desired performance properties.

The following examples are given by way of illustration to further explain the principles of the invention. These examples are merely illustrative and are not to be understood as limiting the scope and underlying principles of the invention in any way. All percentages referred to herein are by weight unless otherwise specifically indicated.

In the following examples and throughout the specification, water dilution percentages are calculated as the amount of water added to dilute the solution divided by the total weight of the diluted solution. For example, if a solution initially weighs 100 grams and 50 grams of water are added to dilute it, the water dilution is 33.33%. Examples 1-17 use commercial grades of neutralized aliphatic alcohol sulfates where the aliphatic radical comprises a mixture of aliphatic chains, with each mixture having a predominant radical which identifies it. The mixture of radicals for the sulfate used in each example is represented by R'. The remaining Examples use commercial grades of the indicated neutralized organic member. Commercial grades of aluminum sulfate are also used in the Examples and all calculations include any water of hydration that may be present in the aluminum sulfate.

EXAMPLE 1

To 11,032.7 g of an aqueous solution containing 27.37% of a commercial grade of sodium lauryl sulfate made from a mixture of $C_{10}$ and $C_{18}$ alcohols having an average chain length of $C_{12}$ and an equivalent weight of 293 is added 8967.3 g of an aqueous solution containing 11.38% of $Al_2(SO_4)_3 \cdot 14H_2O$. The I ratio of the resulting solution is 0.167. The solution is stirred at room temperature for 15 minutes to give a theoretical or theory active solution of 15.0% calculated as aluminum lauryl sulfate and represented as $Al(LS)_3$ at an equivalent weight of 279. The actual active solution is determined by the standard para-toluidine test to be 14.4% calculated as aluminum lauryl sulfate. The final resulting solution is clear, free of precipitate, and has a pH of 3.9. The solution contains a soluble mixed complex aluminum salt which corresponds to the general formula $R'OSO_3Na.O.167Al_2(SO_4)_3 \cdot 14H_2O$, where R' represents the mixture of $C_{10}$ and $C_{18}$ radicals.

A portion of the solution containing 100 g is diluted with 1500 g water representing a 93.75% dilution. An insoluble precipitate forms which is then isolated by filtration. The insoluble precipitate is air dried and weighs 14.3 g on a dry basis. The precipitate is analyzed and has the following composition.

|  | Found |
|---|---|
| R'OSO$_3$ | 86.02% |
| Organic Sulfur | 10.79% |
| Aluminum | 2.82% |
| Inorganic Sulfate | 0.58% |

The analysis established an empirical formula for the precipitate salt of $(R'OSO_3)_4Al.05Na_2SO_4$.

EXAMPLE 2

The procedure of Example 1 is repeated except that 200 g of an aqueous solution containing 34.6% of sodium lauryl sulfate having an equivalent weight of 297.6 is added to 251.6 g of an aqueous solution containing 9.16% of $Al_2(SO_4)_3 \cdot 14H_2O$. The I ratio of the resulting solution is 0.167. The solution is stirred at room temperature to give a theory active solution of 15% calculated as $Al(LS)_3$ at an equivalent weight of 283.6. The final resulting solution is clear, free of precipitate, and has a pH of 3.9. The solution contains a soluble mixed complex aluminum salt which corresponds to the general formula $R'OSO_3Na.\ 0.167Al_2(SO_4)_3 \cdot 14H_2O$.

A portion of the solution containing 100 g is diluted with 1500 g of water representing a 93.75% dilution. An insoluble precipitate forms which is then isolated by filtration. The insoluble precipitate is air dried and weighs 14.4 g on a dry basis. The precipitate is analyzed and has the following composition:

|  | Found |
|---|---|
| R'OSO$_3$ | 84.93% |
| Organic Sulfur | 7.1% |
| Aluminum | 2.84% |
| Inorganic Sulfate | 1.62% |

The analysis established an empirical formula for the precipitate salt of $(R'OSO_3)_3.3Al.0.1Na_2SO_4$.

EXAMPLE 3

The procedure of Example 1 is repeated except that 100 g of an aqueous solution containing 26.9% of sodium oleyl sulfate having an equivalent weight of 362 is added to 72.4 g of an aqueous solution containing 10.22% of $Al_2(SO_4)_3.14H_2O$. The I ratio of the resulting solution 0.167. The solution is stirred at room temperature to give a theory active solution of 15% calculated as aluminum oleyl sulfate. The final resulting solution is clear and free of precipitate. The solution contains a soluble mixed complex aluminum salt which corresponds to the general formula $R'OSO_3Na..167Al_2(SO_4)_3.14H_2O$.

A portion of the solution containing 100 g is diluted with 1500 g of water representing a 93.75% dilution. An insoluble precipitate forms.

EXAMPLE 4

The procedure of Example 1 is repeated except that 189.5 g of an aqueous solution containing 28.5% of sodium lauryl sulfate having an equivalent weight of 305 is added to 49.7 g of an aqueous solution containing 24.25% of $Al_2(SO_4)_3.18H_2O$. The I ratio of the resulting solution is 0.199. The solution is stirred at 45° C for 5 minutes to give a theory active solution of 27.2% calculated as $Al(LS)_3$ at an equivalent weight of 291. The final resulting solution is clear and free of precipitate. The solution contains a soluble mixed complex aluminum salt which corresponds to the general formula $R'OSO_3Na.0.199Al_2(SO_4)_3.18H_2O$.

EXAMPLE 5

The procedure of Example 1 is repeated except that 103.2 g of an aqueous solution containing 28.2% of magnesium lauryl sulfate having an equivalent weight of 291 is added to 88.8 g of an aqueous solution containing 22.9% of $Al_2(SO_4)_3.14H_2O$. The I ratio of the resulting solution is 0.333. The solution is stirred at room temperature for 15 minutes to give a theory active solution of 15% calculated as aluminum lauryl sulfate. The final resulting solution is clear, free of precipitate, and has a pH of 3.1. The solution contains a soluble mixed complex aluminum salt which corresponds to the general formula $(R^1OSO_3)_2 Mg.0.333Al_2(SO_4)_3.14H_2O$.

EXAMPLE 5

The procedure of Example 1 is repeated except that 107 g of an aqueous solution containing 39.4% of triethanolamine lauryl sulfate having an equivalent weight of 422 is added to 79.8 g of an aqueous solution containing 24.81% of $Al_2(SO_4)_3.14H_2O$. The I ratio of the resulting solution is 0.333. The solution is stirred at room temperature to give a theory active solution of 15% calculated as aluminum lauryl sulfate. The final resulting solution is clear, free of precipitate, and has a pH of 3.6. The solution contains a soluble mixed complex aluminum salt which corresponds to the general formula $R^1OSO_3N(C_2H_5O_3).0.333Al_2(SO_4)_3.14H_2O$.

EXAMPLE 7

The procedure of Example 1 is repeated except that 200 g of an aqueous solution containing 27.3% of ammonium lauryl sulfate having an equivalent weight of 293 is added to 1528 g of an aqueous solution containing 13.58% of $Al_2(SO_4)_3.18H_2O$. The I ratio of the resulting solution is 0.167. The solution is stirred at room temperature to give a theory active solution of 15% calculated as aluminum lauryl sulfate. The final resulting solution is clear, free of precipitate, and has a pH of 3.8. The solution contains a soluble mixed complex aluminum salt which corresponds to the general formula $R^1OSO_3NH_4.0.167Al_2(SO_4)_3.18H_2O$.

A 100 g sample of the final solution of Examples 1, 5, 6 and 7 is diluted with water until an insoluble precipitate appears. The specific dilution ratios at which each sample exhibits the formation of an insoluble precipitate is shown in Table 1 below.

TABLE 1

| Example | % Theory Active (Actual) | Cation | % Water dilution for appearance of Insoluble ppt. |
|---|---|---|---|
| 1 | 15(14.4) | Na | 52.4% |
| 7 | 15 | $NH_4$ | 53.3% |
| 5 | 15 | Mg | 68.3% |
| 6 | 15 | $N(C_2H_5O_3)$ | 76.1% |

Table 1 shows that the dilution point at which the mixed salts become insoluble differs depending on the cation of the neutralized alcohol salt.

EXAMPLE 8

This example illustrates the preparation of a mixed complex aluminum salt which is completely soluble in water at any degree of dilution.

The procedure of Example 1 is repeated except that 100 g of an aqueous solution containing 27.0% of ammonium lauryl ether sulfate having one mole of ethylene oxide per mole of ether sulfate and an equivalent weight of 344 is added to 75.3g of an aqueous solution containing 11.55% of $Al_2(SO_4)_3.18H_2O$. The I ratio of the resulting solution is 0.166. The solution is stirred at room temperature to give a theory active solution of 15% calculated as aluminum lauryl ether sulfate. The final resulting solution is clear and free of precipitate. The solution contains a soluble mixed complex aluminum salt which corresponds to the general formula $R^1(OCH_2CH_2)1OSO_3NH_4.0.166Al_2(SO_4)_3.18H_2O$.

A portion of the solution is diluted with water to a 98% dilution to give a clear solution without formation of insoluble precipitate.

EXAMPLE 9

The procedure of Example 8 is repeated except that 100 g of an aqueous solution containing 26.2% of ammonium lauryl ether sulfate having 3.5 moles of ethylene oxide per mole of ether sulfate at an equivalent weight of 451 is added to 71.0 g of an aqueous solution containing 9.01% of $Al_2(SO_4)_3.18H_2O$. The I ratio of the resulting solution is 0.165. The solution is stirred at room temperature to give a theory active solution of 15% calculated as aluminum lauryl ether sulfate. The final resulting solution is clear and free of precipitate. The solution contains a soluble mixed complex aluminum salt which corresponds to the general formula $R^1(OCH_2CH_2)_3.5OSO_3NH_4.0.165Al_2(SO_4)_3.18H_2O$.

A portion of the solution is diluted with water to a 99.3% dilution to give a clear solution without formation of an insoluble precipitate.

EXAMPLE 10

The procedure of Example 8 is repeated except that 100 g of an aqueous solution containing 38.9% ammonium 2-ethyl hexyl ether sulfate having 12 ethoxy groups per mole and an equivalent weight of 780 is added to 156.33 g of an aqueous solution containing 3.15% of $Al_2(SO_4)_3.14H_2O$. The I ratio of the resulting solution is 0.167. The solution is stirred at room temperature to give a theory active solution of 15% calculated as aluminum 2-ethyl hexyl ether sulfate. The final resulting solution is clear and free of precipitate. The solution contains a soluble mixed complex aluminum salt which corresponds to the general formula $R^1(OCH_2CH_2)_{1.2}OSO_3NH_4.0.167Al_2(SO_4)_3.14H_2O$.

A portion of the solution is diluted with water to a 99.3% dilution to give a clear solution without formation of an insoluble precipitate.

EXAMPLE 11

The procedure of Example 8 is repeated except that 177 g of an aqueous solution containing 21.7% of sodium lanolin mixed alcohol ether sulfate having an average of 1.5 ethoxy groups per mole and an equivalent weight of 385 is added to 70.13 g of an aqueous solution containing 28.33% of $Al_2(SO_4)_3.14H_2O$. The ethoxy alcohols comprise a mixture of 16% lanolin, 2% oleyl alcohol, and 59% lauryl alcohol. The I ratio of the resulting solution is 0.333. The solution is stirred at room temperature to give a theory active solution of 15% calculated as aluminum lanolin mixed alcohol ether sulfate salt. The final resulting solution is clear, free of precipitate, and has a pH of 3.5. The solution contains a soluble mixed complex aluminum salt which corresponds to the general formula $R^1(OC_2H_4)_{1.5}OSO_3.Na.0.333Al_2(SO_4)_3.14H_2O$.

A portion of the solution is diluted with water to a 96.87% dilution before any noticeable amount of insoluble precipitate forms

EXAMPLE 12

The procedure of Example 8 is repeated except that 217 g of an aqueous solution containing 28.0% of ammonium myristyl ether sulfate having 3 ethoxy groups per mole and an equivalent weight of 608 is added to 182.9 g of an aqueous solution containing 5.41% of $Al_2(SO_4)_3.14H_2O$. The I ratio of the resulting solution is 0.167. The solution is stirred at room temperature to give a theory active solution of 15% calculated as aluminum myristyl ether sulfate. The final solution is clear and free of precipitate. The solution contains a soluble mixed complex aluminum salt which corresponds to the general formula $R^1(OCH_2CH_2)_6OSO_3NH_4.0.167Al_2(SO_4)_3.14H_2O$.

A portion of the solution is diluted with water to a 95.5% dilution and gives no evidence of insolubility.

EXAMPLE 13

This example illustrates the foaming properties of aqueous solutions containing the salts of the present invention. Foam tests are conducted on the 15% theory active solutions of Examples 1, 5, 6 and 11. The foam test is performed by placing a sample from each solution in a 250 ml graduated cylinder and shaking 50 times. The initial foam heights are reported in Table 2 below as a function of % theory activity of the solution. The solutions of the tested Examples are diluted to various degrees of activity and the initial foam at each degree of activity is reported. The initial foam heights for the salts of Examples 1 and 5 are performed on both the soluble mixed complex form of the salt and on the insoluble form of salt by going through the dilution point at which the insoluble form appears.

TABLE 2

| % Theory Active Solution | Initial Foam Height (ml) Ex. No | | | |
|---|---|---|---|---|
| | 1 | 5 | 6 | 11 |
| As is 15% | 40 | 80 | 100 | 100 |
| 13.5% | 87 | 127 | 127 | 127 |
| 12.0% | 123 | 153 | 163 | 153 |
| 9.0% | 200 | 200 | 210 | 210 |
| 7.5% | 230 | 240 | 270 | 246 |
| 6.0% | 205* | 205 | 205 | 205 |
| 4.5% | 277 | 277* | 267 | 267 |
| 1.5% | 180 | 150 | 160 | 280 |
| .075% | 160 | 140 | 150 | 280 |

* = Appearance of insoluble form.

EXAMPLE 14

The compatibility of the active solutions of this invention with a foam booster is tested by adding 100 g of the 15% theory active solution of Example 12 to 5 g of a coconut monoethanolamide, a known foam booster. The resultant product is a clear viscous liquid. A sample of the liquid is diluted to a 95.5% dilution with water and no evidence of insoluble precipitates is observed.

EXAMPLE 15

A 100 g solution containing a sodium lauryl sulfate/amide blend is prepared by mixing 81.5 g of an aqueous solution containing 28.5% sodium lauryl sulfate having an equivalent weight of 305 with 7.33 g of a coco monoethanolamide and sufficient water to form 100 g of solution. To this 100 g solution is added 47.4 g of an aqueous solution containing 15.82% $Al_2(SO_4)_3.14H_2O$. The I ratio of the resulting solution is 0.166. The resulting solution is a clear viscous liquid and can be diluted to a water dilution of 75.6% before an insoluble form appears.

EXAMPLE 16

To 100 g of the 15% theory active solution of Example 9 is added 5 g of coco monoethanolamide. The resultant solution is a clear viscous liquid. A sample is diluted with water to a 95.0% water dilution. The sample gives no evidence of any insoluble precipitate.

EXAMPLE 17

In accordance with the procedure of Example 13, foam tests are performed on the salts of Examples 12, 14, 3 15 and 16. The tests are conducted on solutions containing 0.75% active salt as aluminum alkyl or alkyl ether sulfate at 40° C. The initial foam height and the height after 1 minute intervals are reported in Table 3 below.

TABLE 3

| Salt of Example No. | Foam Height (ml) v time (min) | | | |
|---|---|---|---|---|
| | 0 min. | 1 min. | 2 min. | 3 min. |
| 12 | 200 | 184 | 165 | 160 |
| 14 | 255 | 242 | 234 | 218 |
| 3 | 160 | 141 | 124 | 120 |
| 15 | 218 | 206 | 186 | 170 |
| 16 | 250 | 240 | 234 | 227 |

EXAMPLE 18

An 11.4% aqueous solution containing 50 g of $Al_2(SO_4)_3.14H_2O$ (0.084 mole) was added to 541 g (0.387 mole) of a 25.7% aqueous solution of sodium lauryl propoxy sulfate, $C_{12}H_{25}(OCH_2(CH_3)CH)SO_4Na$. The solution was stirred at ambient temperature for 15 minutes to give a theory active solution of 13.6% calculated as aluminum lauryl propoxysulfate, representing an equivalent weight of 346. The actual active solution was determined by the standard para-toluidine test to be 13.2% calculated as aluminum lauryl propoxysulfate. The resulting solution is clear, free of precipitate, has a pH of 3.9 and contains a soluble mixed complex aluminum salt which corresponds to the general formula $$R' - O - SO_3Na \cdot 0.21\ Al_2(SO_4)_3 \cdot 14H_2O$$

in which R' represents a mixture of propoxylated $C_{10}$ to $C_{18}$ radicals. The I ratio was calculated at 0.217.

EXAMPLE 19

The procedure of Example 18 was repeated except that a solution of 33 g $Al_2(SO_4)_3 \cdot 14H_2O$ in 33 g water was heated to 80°–90° C and added to 1552 g of a 14.9% active solution of sodium Pluronic L-64 sulfate. Pluronic L-64 is an ethylene oxide-propylene oxide block polymer with a total M.W. of 2900. The solution was a clear liquid with an I ratio of 0.167 per organic sulfate. A sample of the complex was diluted to less than 0.1% without precipitation and contains a soluble mixed complex aluminum salt which corresponds to the general formula $$0.167[Al_2(SO_4)_3 \cdot 14H_2O] \cdot NaSO_4(C_2H_4O)13(C_3H_6O)_{30}(C_2H_4O)_{13}SO_3Na \cdot 0.167[Al_2(SO_4)_3 \cdot 14H_2O]$$

EXAMPLE 20

The procedure of Example 18 was repeated except that a solution of 100 g of aluminum sulfate tetradecahydrate in 778 g water was added at 25° C to 1082 g of 30% active manganese lauryl sulfate. There was obtained 1960 g of clear 16.5% active manganese lauryl sulfate-aluminum sulfate complex based on an equivalent weight of 313 for manganese lauryl sulfate. A sample of this complex solution precipitated upon dilution to 6.5% active.

EXAMPLE 21

The procedure of Example 18 was repeated except that 9.9 g of $Al_2(SO_4)_3 \cdot 14H_2O$ in 233.3 g water was added at 25° C with constant stirring to 86.8 g of a 58% active solution of nonyl phenoxyethoxy ammonium sulfate,

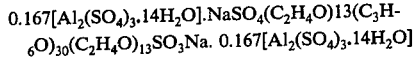

$$C_9H_{19} - \langle \rangle - (O-CH_2CH_2)_{4.25} - OSO_3NH_4,$$

traded commercially as Alipal CO-436. There was obtained 330 g of a 15% active complex based on an equivalent weight of 495. This complex precipitated upon a 94.1% dilution of the 15% active material.

EXAMPLE 22

The procedure of Example 18 was repeated except that a solution of 50 g of $Al_2(SO_4)_3 \cdot 14H_2O$ in 389 g water was added to 541 g of 30% active solution of potassium toluene sulfonate. The resultant clear solution contained 11.5% aluminum toluene sulfonate at an equivalent weight of 181.

EXAMPLE 23

The procedure of Example 18 was repeated except that 9.9 g of aluminum sulfate tetradecahydrate in 55 g water was added to 158.2 g of 22% sodium dodecyl benzene sulfonate at 90° C. The complex precipitated as a white paste at ambient temperatures and contained 14.9% aluminum alkylaryl sulfonate complex. The precipitate was soluble at 90° C.

EXAMPLE 24

The procedure of Example 18 was repeated except that a solution of 9.9 g of aluminum sulfate tetradecahydrate in 56.9 g water was added to 219 g of a 20.3% solution of dioctyl sodium sulfosuccinate at 90° C. There was obtained 286 g of 15% active aluminum dioctyl sulfosuccinate at equivalent weight 430. Dilution of this complex to 1% formed on insoluble precipitate, however, a 1% solution of the non-complexed dioctyl sodium sulfosuccinate was completely soluble.

EXAMPLE 25

The procedure of Example 18 was repeated except that a solution of 50 g of $Al_2(SO_4)_3 \cdot 14H_2O$ in 389 g water was added to 541 g of a 30% active disodium alkylethoxy sulfosuccinate (available from American Cyanamide as Aerosol 102). The product was a clear solution containing the aluminum complex which did not precipitate upon dilution to less than 1% active.

EXAMPLE 26

The procedure of Example 18 was repeated except that 5.0 g of aluminum sulfate tetradecahydrate was dissolved in 38.9 g water and added to 54.1 g of a stirred 25% solution of sodium N-methyl N-coconut oil taurate at 50° C. The aluminum complex was a clear solution which precipitated upon dilution to 4.4% activity.

EXAMPLE 27

The procedure of Example 18 was repeated except that 5.0 g of aluminum sulfate tetradecahydrate was dissolved in 38.9 water and added to 54.1 g of a 30% solution of sodium coconut oil isethionate. The resulting 16.5% active aluminum complex was soluble at less than 1% active.

EXAMPLE 28

This example illustrates that the mixed complex organic aluminum salts of the present invention cannot be prepared from all neutralized salts having an anionic molity.

To a solution of 100 g alkylethoxyphosphate (available from GAF as Gafac RA-600) in 204 g water and neutralized to pH 4.75 with 18.3 g of 50% caustic soda was added at 60° C 11.0 g $Al_2(SO_4)_3 \cdot 14H_2O$ dissolved in 11 g water. The mixture immediately turned to an insoluble paste. The I ratio was 0.167. A soluble complex was not formed.

EXAMPLE 29

The procedure of Example 28 was repeated except that to 200 g of a 50% active solution of nonylphenolethoxy phosphate (Gafac RE-610) neutralized to pH 4.75 with 11.7 g of 50% caustic solution was added at 60° C 11.0 g $Al_2(SO_4)_3 \cdot 14H_2O$ dissolved in 15.3 g water. At this I ratio of 0.167 an insoluble paste was formed.

The invention in its broader aspects is not limited to the specific details shown and described and departures may be made from such details without departing from the principles of the invention and without sacrificing its chief advantages.

What is claimed is:

1. An aqueous solution of from about 10 weight % to about 60 weight % of a soluble mixed complex salt of aluminum sulfate and a neutralized organic salt selected from the group consisting of:

(a) an aliphatic alcohol sulfate; an alkylaryl sulfate, an alkyl, aryl or alkyaryl sulfonate; a sulfosuccinate; an N-acyl-N-alkyl taurate; and a sulfoalkyl ester of a fatty acid; which mixed complex salt has the formula:

$$[R—(OC_yH_{2y})_n—A_m—(O)_p—SO_3]_x m.I[Al_2(SO_4)_3]$$

in which R is an aliphatic radical containing 1 to 30 carbon atoms or alkylaryl hydrophobic residue having an alkyl radical containing 1 to 30 carbon atoms; $n$ is the number of alkylene oxide groups and can be from 0 to about 100; $y$ is a number from 2 to 4; A is a radical selected from the group consisting of

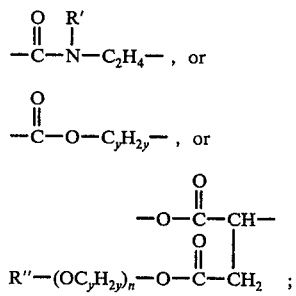

in which R′ is H or an alkyl group of 1 to 4 carbon atoms; R″ is an alkali metal or an alkyl group having from 8 to 22 carbon atoms; $m$ and $p$ are each the numbers 0 or 1, M is a cation having a valence of $x$, and is selected from the group of alkali metal, alkaline earth metal, manganese, zinc, copper, iron, cobalt, nickel, or nitrogen containing base radicals; $x$ is the hydrogen equivalence value of M and can be 1 or 2; and I can be a number from about 0.001 to about 6; and (b) a sulfated ethylene oxide-propylene oxide block polymer, which mixed salt has the formula:

I $$Al_2(SO_4)_3.M_d[(H)_f(SO_4)_d(C_2H_4O)_a(C_3H_6O)_b(C_2H_4O)_c(SO_3)_e H_g]_x M_e.I\ Al_2(SO_4)_3$$

in which $b$ is an integer from 15 to 60; $a$ and $c$ are each at least 1 and $a+c$ is an integer from 4 to 300; M, $x$ and I are as defined above; $f+d$ and $e+g$ are equal to 1; and $d$ and $e$ are each a number from 0.1 to 1.0.

2. The aqueous solution of claim 1, wherein said mixed salt is of aluminum sulfate and an aliphatic alcohol sulfate or an alkylaryl hydrophobe sulfate, and said soluble mixed complex salt has the formula: $[R—(OC_yCH_{2y})_n—OSO_3]_x M.I[Al_2(SO_4)_3]$ in which R represents the residue of an aliphatic alcohol or an alkylaryl hydrophobe having from 1 to 30 carbon atoms; $n$ is a number from 1 to 100; $y$ is a number from 2 to 4; M is a cation having a valence of $x$ selected from the group consisting of alkali metal, alkaline earth metal, manganese, zinc, copper, iron, cobalt, nickel, and nitrogen containing base radicals, $x$ is the hydrogen equivalence value of M and can be 1 or 2, and I is a number from 0.001 to 6.

3. The aqueous solution of claim 2, wherein I is from 0.167 to 1.

4. The aqueous solution of claim 2, wherein R is a lauryl, oleyl, 2-ethyl hexyl, myristyl, nonyl phenoxyethoxy radical.

5. The aqueous solution of claim 2, wherein R is an alkyl group of from 8 to 22 carbon atoms.

6. The aqueous solution of claim 2, wherein $n$ is from 0.5 to 100.

7. The aqueous solution of claim 2, wherein $m$ is 1.

8. The aqueous solution of claim 2, wherein $n$ is from 1 to 50.

9. The aqueous solution of claim 2, wherein $n=0$.

10. The aqueous solution of claim 2, wherein $m=0$.

11. The aqueous solution of claim 2, wherein the amount of complex salt is between about 10 weight % and 35 weight %, based on the weight of the solution.

12. The aqueous solution of claim 2, wherein M is selected from the group consisting of sodium, potassium, ammonium, magnesium, manganese, and alkyol amines.

13. The aqueous solution of claim 1, wherein the said complex salt is of aluminum sulfate and a neutralized dialkyl sulfosuccinate.

14. The aqueous solution of claim 1, wherein said complex salt is aluminum sulfate and a neutralized alkylethoxysulfosuccinate.

15. The aqueous solution of claim 1, wherein said complex salt is of aluminum sulfate and a neutralized alkyl, aryl, or alkylaryl sulfonate.

16. The aqueous solution of claim 1, wherein said complex salt is of aluminum sulfate and a neutralized N-acyl-N-alkyl taurate.

17. The aqueous solution of claim 1, wherein said complex salt is of aluminum sulfate and a neutralized sulfoalkyl ester of a fatty acid.

18. The aqueous solution of claim 1, wherein said complex salt is of aluminum sulfate and a neutralized, sulfated ethylene oxide-propylene oxide block polymer, and said soluble mixed complex salt has the formula: I $AL_2(SO_4)_3.M_d[(H)_f\ (SO_4)_d(C_2H_4O)_a(C_3H_6O)_b(C_2H_4O)_c(SO_3)_e H_g]_x M_e.I\ Al_2(SO_4)_3$ in which $b$ represents an integer from 15 to 60; $a$ and $c$ are each at least 1 and $a+c$ represents an integer from 4 to 300; $f+d$ and $e+g$ equal 1; $d$ and $e$ represent a number from 0.1 to 1; M represents a cation having a valence of $x$ selected from the group consisting of alkali metal, alkaline earth metal, manganese, zinc, copper, iron, cobalt, nickel, and nitrogen containing base radicals, $x$ is the equivalent value of M and can be 1 or 2; and I is a number from 0.001 to 6.

* * * * *